(12) United States Patent
Neumann (10) Patent No.: US 11,075,001 B1
(45) Date of Patent: Jul. 27, 2021

(54) METHODS AND SYSTEMS FOR ORDERED FOOD PREFERENCES ACCOMPANYING SYMPTOMATIC INPUTS

(71) Applicant: KPN Innovations, LLC, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 0 days.

(21) Appl. No.: 16/887,319

(22) Filed: May 29, 2020

(51) Int. Cl.
| | |
|---|---|
| *G06Q 30/00* | (2012.01) |
| *G16H 20/60* | (2018.01) |
| *G16H 10/60* | (2018.01) |
| *G16H 50/20* | (2018.01) |
| *G06N 20/00* | (2019.01) |
| *G06Q 10/08* | (2012.01) |
| *G06Q 30/06* | (2012.01) |
| *G06F 16/2457* | (2019.01) |
| *G16H 70/60* | (2018.01) |

(52) U.S. Cl.
CPC ....... *G16H 20/60* (2018.01); *G06F 16/24578* (2019.01); *G06N 20/00* (2019.01); *G06Q 10/0875* (2013.01); *G06Q 30/0633* (2013.01); *G16H 10/60* (2018.01); *G16H 50/20* (2018.01); *G16H 70/60* (2018.01)

(58) Field of Classification Search
CPC ........ G16H 20/60; G16H 70/60; G16H 10/60; G16H 50/20; G06N 20/00; G06F 16/24578; G06Q 10/0875; G06Q 30/0633

USPC ..................................................... 705/26, 27
See application file for complete search history.

(56) References Cited

U.S. PATENT DOCUMENTS

| | | | |
|---|---|---|---|
| 8,725,590 B2 | 5/2014 | Lipscher | |
| 8,918,355 B2 | 12/2014 | Perrier | |
| 9,070,175 B2 | 6/2015 | Hurst | |
| 10,366,434 B1 * | 7/2019 | Belousova | ............. G06Q 50/12 |
| 2001/0025279 A1 | 9/2001 | Krulak | |
| 2014/0080102 A1 | 3/2014 | Krishna | |

(Continued)

OTHER PUBLICATIONS

"Innit Launches App to Revolutionize The Way We Eat: The Innit App Helps Consumers Plan, Shop, Prepare, and Cook Delicious Meals Every Day," PR Newswire, Dec. 5, 2017, Dialog #1972186899, 3pgs. (Year: 2017).*

*Primary Examiner* — Robert M Pond
(74) *Attorney, Agent, or Firm* — Caldwell Intellectual Property Law, LLC (57) ABSTRACT

A system for ordered food preferences accompanying symptomatic inputs, the system including a computing device configured to receive a symptomatic input relating to a user wherein the symptomatic input includes a description of a symptomatic complaint; generate a machine-learning process, wherein the machine-learning process is trained using a first training set relating symptomatic inputs to symptomatic neutralizers; identify a symptomatic neutralizer based on the symptomatic input using the machine-learning process; generate an ordered food element list wherein the ordered food element list ranks food elements as a function of the symptomatic neutralizer; and create a food preference menu for the user wherein creating the food preference menu further comprising grouping the ordered food elements.

16 Claims, 5 Drawing Sheets

(56) References Cited

U.S. PATENT DOCUMENTS

| | | | |
|---|---|---|---|
| 2014/0236622 A1* | 8/2014 | Southam | G06Q 10/04 705/2 |
| 2014/0287384 A1 | 9/2014 | Boyes | |
| 2015/0243186 A1 | 8/2015 | Eberhardt et al. | |
| 2016/0078182 A1* | 3/2016 | Allen | G16H 50/30 702/19 |
| 2018/0075218 A1* | 3/2018 | Benefield | G16H 70/20 |
| 2018/0240359 A1* | 8/2018 | Hujsak | G06F 16/2455 |
| 2019/0228856 A1* | 7/2019 | Leifer | G16H 20/60 |
| 2019/0304000 A1* | 10/2019 | Simpson | G01N 33/492 |
| 2020/0074884 A1 | 3/2020 | Murdoch et al. | |
| 2020/0219605 A1* | 7/2020 | Govindjee | G16H 50/20 |
| 2020/0265525 A1* | 8/2020 | Chatman | G06Q 40/12 |

* cited by examiner

METHODS AND SYSTEMS FOR ORDERED FOOD PREFERENCES ACCOMPANYING SYMPTOMATIC INPUTS

FIELD OF THE INVENTION

The present invention generally relates to the field of nourishment. In particular, the present invention is directed to methods and systems for ordered food preferences accompanying symptomatic inputs.

BACKGROUND

Food element preferences can change over time. In addition, various features can affect food element preferences. Utilizing food preferences in combination with selecting food elements that minimize symptomatic inputs remain to be seen.

SUMMARY OF THE DISCLOSURE

In an aspect, a system for ordered food preferences accompanying symptomatic inputs, the system comprising a computing device, the computing device designed and configured to receive a symptomatic input relating to a user wherein the symptomatic input includes a description of a symptomatic complaint; generate a machine-learning process, wherein the machine-learning process is trained using a first training set relating symptomatic inputs to symptomatic neutralizers; identify a symptomatic neutralizer based on the symptomatic input using the machine-learning process; generate an ordered food element list wherein the ordered food element list ranks food elements as a function of the symptomatic neutralizer; and create a food preference menu for the user wherein creating the food preference menu further comprising grouping the ordered food elements.

In an aspect, a method of ordered food preferences accompanying symptomatic inputs the method comprising receiving by a computing device, a symptomatic input relating to a user wherein the symptomatic input includes a description of a symptomatic complaint; generating by the computing device, a machine-learning process, wherein the machine-learning process is trained using a first training set relating symptomatic inputs to symptomatic neutralizers; identifying by the computing device, a symptomatic neutralizer based on the symptomatic input using the machine-learning process; generating by the computing device, an ordered food element list wherein the ordered food element list ranks food elements as a function of the symptomatic neutralizer; and creating by the computing device, a food preference menu for the user wherein creating the food preference menu further comprising grouping the ordered food elements.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for ordered food preferences accompanying symptomatic inputs. In an embodiment, symptomatic input is utilized to generate a food preference menu. Genetic food preferences are utilized in combination with a machine-learning process to identify food preferences, and rank food elements utilizing such information.

Figure 1:
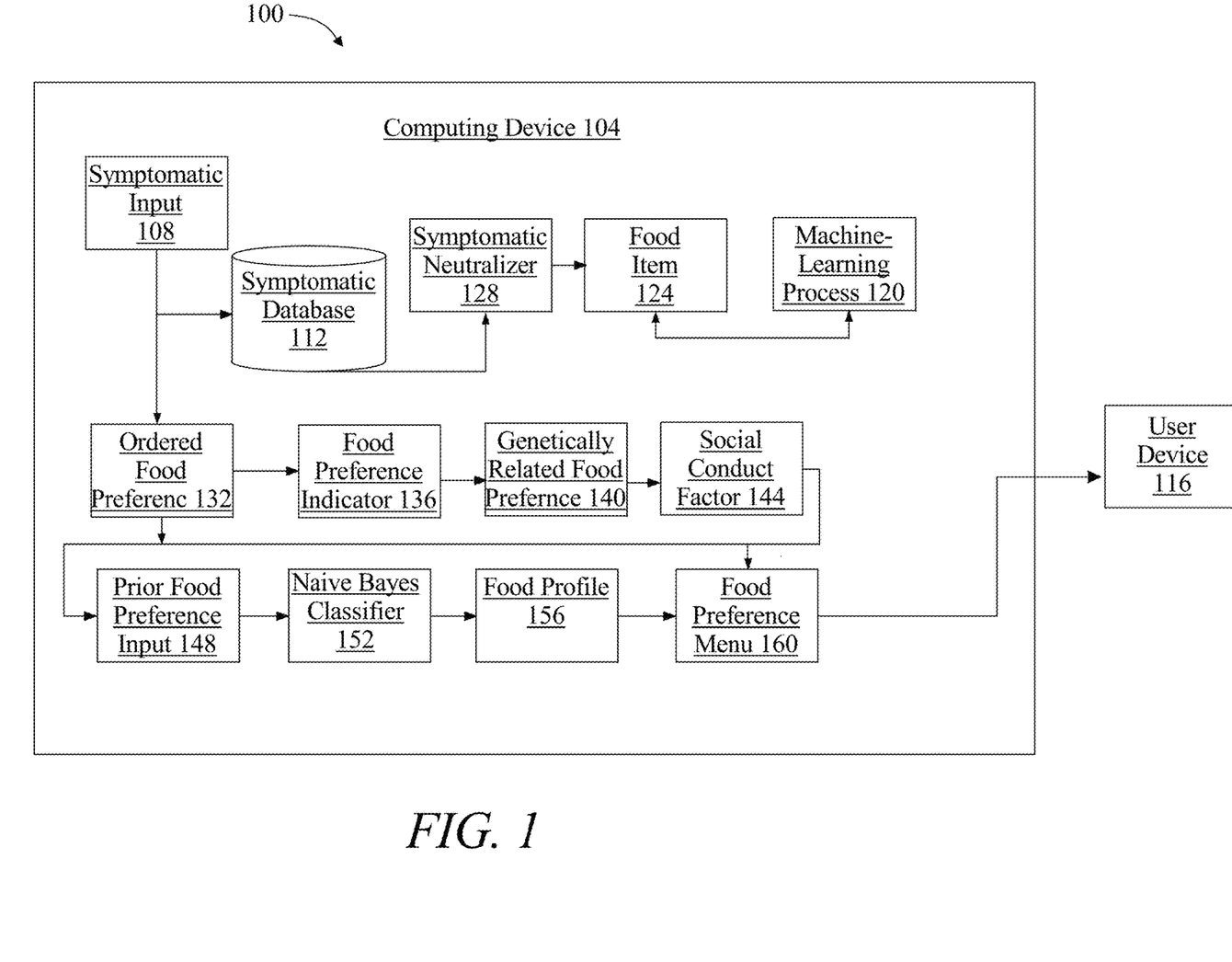
FIG. 1 is a block diagram illustrating an exemplary embodiment of a system for ordered food preferences accompanying symptomatic inputs.

Referring now to FIG. 1, an exemplary embodiment of a system 100 for ordered food preferences accompanying symptomatic inputs is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or connect with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or connect with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be transmitted to and/or from a computer and/or a computing device 104. Computing device 104 may include but is not limited to, for example, a computing device 104 or cluster of computing devices 104 in a first position and a second computing device 104 or cluster of computing devices 104 in a second position. Computing device 104 may include one or more computing devices 104 dedicated to data storage, security, dispersal of traffic for load balancing, and the like. Computing device 104 may distribute one or more computing tasks as described below across a plurality of computing devices 104 of computing device 104, which may operate in parallel, in series, redundantly, or in any other manner used for dispersal of tasks or memory between computing devices 104. Computing device 104 may be implemented using a "shared nothing" architecture in which data is cached at the operative, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a symptomatic input 108 relating to a user. A "symptomatic input," as used in this disclosure, is a description of any physical and/or mental feature of a user that may indicate a condition and/or disease. A symptomatic input 108 includes a description of a symptomatic complaint. A "symptomatic complaint," as used in this disclosure, is a description of any symptom a user has previously or is currently experiencing. A symptomatic complaint may include a symptom of a disease that a user experiences, such as a user who experiences joint pain and fatigue from rheumatoid arthritis. In yet another non-limiting example, a symptomatic complaint may contain a description of symptoms that a user who was previously diagnosed with fibroids experiences which includes heavy menstrual bleeding, pelvic pressure, and frequent urination. A symptomatic input may include a subjective symptom such as tiredness. A symptomatic input 108 may include an objective symptom such as a cough. A symptomatic input 108 may indicate a physiological state of a user, such as a pregnant female who complains of morning sickness. A symptomatic input 108 may describe a brief acute symptom, such as a back spasm that comes on suddenly. A symptomatic input 108 may describe a chronic symptom, such as a dry cough and chest congestion that occurs every morning upon waking. A symptomatic complaint may include a description of one or more general symptoms that affect the entire body such as fever, malaise, anorexia, and weight loss.

With continued reference to FIG. 1, a symptomatic complaint may include a diagnosis. A "diagnosis," as used in this disclosure, is a disease, syndrome, condition, disorder, sickness, ailment, and the like identified by a professional. A "professional," as used in this disclosure, is any person with valid credentials and/or certifications to provide wellness services to natural persons. A professional may include a physician, a dentist, a nurse, a chiropractor, an optometrist, a physical therapist, an occupational therapist, a dietician, a nurse practitioner, a psychologist, a licensed professional counselor, a licensed marriage and/or family therapist, a pharmacist, a speech therapist and the like. A diagnosis may include a current condition that a user suffers from, such as ulcerative colitis. A diagnosis may include an impending condition that a user may be at danger of developing due to one or more features, such as heart disease or Type 2 Diabetes Mellitus. A diagnosis may include a condition that was cured and/or resolved, such as an ear infection or a meningitis. A diagnosis may be self-reported by a user, such as a user who self-reports a previous diagnosis of hypertension that a user is currently treating with a drug. A symptomatic input 108 may include an element of previous physical data. An "element of previous physical data," as used in this disclosure, is any previous therapeutic and/or wellness information unique to a user. An element of previous physical data may include demographic information that may include a user's name, gender, age, birthday, occupation, family structure, living arrangements, marital status, and the like. An element of previous physical data may include information regarding any information regarding symptomatic complaints regarding specific body systems such as the head, eyes, ears, nose, and throat (HEENT), cardiovascular, respiratory, gastrointestinal, genitourinary, integumentary, musculoskeletal, endocrine, nervous system, mental, and the like. An element of previous physical data may relate to information describing a user's social well-being and social life, family history, mental or emotional illness or stresses, detrimental or beneficial habits, social life, smoking or exercise habits, educational level, previous surgical history, previous procedures, culture, sexuality, nutrition, spirituality, and the like. An element of previous physical data may relate to past wellness history such as allergies, serious or chronic illnesses, recent hospitalizations, recent surgical procedures, current drugs, alcohol consumption, marijuana use and the like. An element of previous physical data may be received based on one or more questions and/or self-assessments completed by a user.

With continued reference to FIG. 1, information pertaining to a symptomatic input 108 may be stored within symptomatic database 112. Symptomatic database 112 may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, computing device 104 may receive a symptomatic input 108 relating to a user from a user device 116 operated by a user. A user device 116 may include without limitation, a display in communication with computing device 104, where a display may include any display as described herein. A user device 116 may include an additional computing device, such as a mobile device, laptop, desktop, computer, and the like.

With continued reference to FIG. 1, computing device 104 is configured to generate a machine-learning process, wherein the machine-learning process is trained using a first training set relating symptomatic inputs to symptomatic neutralizers. A "machine-learning process," as used in this disclosure, is a process that automatedly uses a body of data known as "training data" and/or a "training set" to generate an algorithm that will be performed by computing device 104 and/or a module to produce outputs given data provided as inputs; this is in contrast to a non-machine learning software program where the commands to be executed are determined in advance by a user and written in a programming language. "Training data," as used in this disclosure, is a set of examples that contain pairs of an input and a corresponding output, which are used to model relationships between two or more categories of data elements. Training data may be formatted to include labels, for instance by associating data elements with one or more descriptors corresponding to categories of data elements. Training data may not contain labels, where training data may not be formatted to include labels. A machine-learning process 120 may include calculating one or more machine-learning algorithms and/or producing one or more machine-learning models. A machine-learning process 120 may include a supervised machine-learning process 120 that applies learned associations from the past to new data using labeled training data to predict future events. A supervised machine-learning process 120 produces an inferred function to make predictions about output values. A supervised machine-learning process 120 may include for example, active learning, classification, regression, and/or similarity learning. A machine-learning process 120 may include an unsupervised machine-learning process 120 where training data utilized to train the unsupervised machine-learning process 120 may not be classified or labeled. An unsupervised machine-learning process 120 may infer a function to describe a hidden structure from unlabeled data. An unsupervised machine-learning process 120 may include for example, clustering, anomaly detection, neural networks, latent variable models, and the like. A machine-learning process 120 may include a semi-supervised machine-learning process 120 that may utilize a combination of both labeled and unlabeled training data. A semi-supervised machine-learning process 120 may include generative models, low density separation, graph-based methods, heuristic approaches, and the like. A machine-learning process 120 may be implemented as any machine-learning process, including for instance, and without limitation, as described in U.S. Nonprovisional application Ser. No. 16/375,303, filed on Apr. 4, 2019, and entitled "SYSTEMS AND METHODS FOR GENERATING ALIMENTARY INSTRUCTION SETS BASED ON VIBRANT CONSTITUTIONAL GUIDANCE," the entirety of which is incorporated herein by reference.

With continued reference to FIG. 1, training data utilized to train a machine-learning process 120 may be obtained from records of previous iterations of a machine-learning process 120, user inputs and/or questionnaire responses, expert inputs, open source platforms and the like. Computing device 104 trains a machine-learning process 120 including any machine-learning algorithm and/or any machine-learning model utilizing a first training set relating symptomatic inputs to food preferences.

With continued reference to FIG. 1, computing device 104 is configured to identify a symptomatic neutralizer based on a symptomatic input using a machine-learning process. A "food element," as used in this disclosure, is any food, beverage, drink, snack, nutritional supplement, and the like intended for consumption by a human being. A "symptomatic neutralizer," as used in this disclosure, is any indication as to how much or how little a food element 124 helps alleviate or exacerbate a symptomatic input 108. For instance and without limitation, a food element 124 such as organ meats may exacerbate a condition of gout, while a food such as sauerkraut may alleviate symptoms associated with a condition such as irritable bowel syndrome. A symptomatic neutralizer may be expressed as a quantitative datum, containing a numerical score that indicates how much or how little a food element alleviates or exacerbates a symptomatic input 108. A symptomatic neutralizer may be expressed on a numerical score from 0 to 100 for example, where a score of 0 may indicate a food element that exacerbates a symptomatic input, while a score of 100 may indicate a food element that alleviates a symptomatic input. For instance and without limitation, a symptomatic neutralizer for a food element such as tomatoes may contain a quantitative datum containing a numerical score of 17 for exacerbating symptoms of a stomach ulcer, while a symptomatic neutralizer for a food element such as honey may contain a quantitative datum containing a numerical score of 77 for alleviating symptoms of a stomach ulcer. Computing device 104 generates a symptomatic neutralizer utilizing one or more regression processes, including any of the regression processes as described herein.

With continued reference to FIG. 1, computing device 104 is configured to generate an ordered food preference 132. An "ordered food preference," as used in this disclosure, is a list of food element 124 ranked based on how well each food element 124 diminishes a symptomatic input 108. A food element 124 may help diminish a symptomatic input 108 when the food element 124 helps alleviate, lessen, treat, and/or mitigate a symptomatic input 108. Food element 124 may be ranked in descending order, whereby food element 124 that help diminish a symptomatic input 108 the most are ranked first, and those that worsen a symptomatic input 108 are ranked last. For instance and without limitation, a symptomatic input 108 that contains a diagnosis of a urinary tract infection may be utilized to generate an ordered food preference 132 that specifies a food element 124 such as raw cranberries as having a high ranking and being able to diminish symptoms of a urinary tract infection, while a food element 124 such as cranberry juice cocktail beverage may have a very low ranking as it contains high levels of high fructose corn syrup that will exacerbate and worsen symptoms of a urinary tract infection. In yet another non-limiting example, a symptomatic input containing a user with an increased risk of developing breast cancer, may contain an ordered food preference 132 that specifies a food element 124 such as all cruciferous vegetables including broccoli, Brussel sprouts, cauliflower, cabbage, bok choy, radish, arugula, and kohlrabi as having a high ranking and reducing a user's risk of developing breast cancer, while a food element 124 such as red meat may exacerbate a user's risk of developing breast cancer.

With continued reference to FIG. 1, computing device 104 generates an ordered food preference 132 utilizing a food preference indicator 136. A "food preference indicator," as used in this disclosure, is any evaluative attitude that a user expresses towards any food element 124. A food preference may include a qualitative evaluation of foods and beverages, indicating how much a user likes or dislikes them. A food preference may be determined based on a hedonic scale, indicating how much a user likes a food or how much a user dislikes a food. A food preference may be determined on a preferred frequency scale, such as how often does a user eat or consume a particular food or beverage. A food preference may be based on a numerical scale, indicating on a scale from 0 to 10 how much a user likes or dislikes a food, where a score of 0 indicates a food that a user does not like and 10 indicates a food that a user does like. One or more food preference indicator 136 may be stored in symptomatic database 112, as described above in more detail. For instance and without limitation, a food preference indicator 136 may specify that a user prefers to consume vegetables that include carrots, celery, and romaine lettuce, but the user does not like to consume Brussel sprouts or cabbage. In yet another non-limiting example, a food preference indicator 136 may specify that a user dislikes all animal products and enjoys consuming gluten free vegan foods. Computing device 104 utilizes a food preference to generate an ordered food element list. For instance and without limitation, computing device 104 may rank a food element 124 contained within an ordered food element list higher when the food element 124 is a food element 124 the user likes to consume, and the food element 124 is a symptomatic neutralizer. In yet another non-limiting example, computing device 104 may rank a food element 124 lower when a food element 124 is a food element 124 that the user does not like to consume and the food element 124 is a symptomatic neutralizer 128, because the user is most likely not going to consume the food element 124.

With continued reference to FIG. 1, computing device 10 is configured to identify an element of data containing a genetically related food preference 140 for a user. A "genetically related food preference," as used in this disclosure, is any genetic indication and/or predisposition that affects a user's food preferences and/or food element 124 tastes. A genetic indication may include the absence and/or presence of any genes that may control a user's food preferences. For instance and without limitation, a user's taste preferences for foods that are sweet tasting may be implicated by genes that are involved in glucose metabolism including but not limited to, TAS1R1, TAS1R2, TAS1R3, SLC2A2, ADIPOQ, ANKK1, DRD2, OPRM1, LEP, LEPR, NPY1 and the like. In yet another non-limiting example, a user's taste preferences for foods that contain fats may be controlled by polymorphisms in the CD36 gene that encode fatty acid translocase, as well as genes that affect regulation of lipolysis and thermogenesis, lipoprotein metabolism, neurotransmission, and signaling regulation such as but not limited to, ADRB3, APOA2, OPRM1, RGS6 and the like. One or more genetically related food preferences pertaining to a user may be stored in symptomatic database 112. Computing device 104 utilizes a genetically related food preference 140 to generate an ordered food preference 132. For example, a food element 124 such as coffee may be ranked higher for a user with a genetically related food preference 140 for bitter foods as affected by the TAS2R38 gene, as compared to a user who does not have a genetically related food preference 140 for bitter foods. In yet another non-limiting example, a food element 124 containing a savory food element 124 such as green cabbage may be ranked higher for a user with a genetically related food preference 140 for umami foods as affected by a GNAT3 gene co-expressed with TAS1R1 gene, as compared to a user who does not have co-expression of the GNAT3 gene and the TAS1R1 gene.

With continued reference to FIG. 1, computing device 104 generates an ordered food preference 132 utilizing a social conduct factor 144. A "social conduct factor," as used in this disclosure, is any social impact on a user's food preferences. A social impact may include any foods and/or cuisines that a user was exposed to as a child, and that shaped a user's food preferences. For instance and without limitation, a user who was brought up in a household eating only vegetarian meals may not eat meat or feel comfortable eating food element 124 that contain meat. A social impact may include any food behaviors and/or food preferences that a user developed based on food element 124 that a family member or friend likes. For example, a husband may learn over time to enjoy food element 124 that his wife enjoys such as fresh salads or meal that contain chicken as compared to beef. In yet another non-limiting example, a user who lives with multiple friends together may learn over time to enjoy food element 124 that the user's friends also like. A social influence may include any influences regarding types of food element 124 that a user consumes. For example, a user who routinely eats out at restaurants and who doesn't cook meals at home may be more adventurous regarding food items and may consume a wider variety of food element 124 as compared to someone who exclusively cooks meals at home. A social influence may include any social eating patterns or eating habits that a user has developed. For example, a user who works very long hours may skip breakfast and only eat two meals each day. Computing device 104 utilizes a social conduct factor 144 to rank food element 124. For example, a social conduct factor 144 that indicates a user doesn't eat breakfast may be utilized to rank food element 124 much lower that are typically food element 124 consumed for breakfast such as oatmeal, eggs benedict, pancakes, donuts, and bacon. One or more social impacts may be stored within symptomatic database 112.

With continued reference to FIG. 1, computing device 104 is configured to receive a prior food preference input 148. A "prior food preference input," as used in this disclosure, is a description of any previous food element 124 that a user has consumed. A prior food preference input 148 may contain a description of a food element 124 that a user consumed, such as a snack containing almonds that a user ate. A prior food preference input 148 may contain a description of a meal that a user consumed, such as a meal containing grilled flank steak served on a bed of arugula and with a side of avocado. A prior food preference input 148 may contain a description of a user's previous eating patterns, such as a description of certain cuisines that a user enjoys eating, including Italian inspired meals or Japanese meals. A prior food preference input 148 may be stored within symptomatic database 112. Computing device 104 classifies using a Naïve Bayes classifier, a prior food preference input 148 to a food profile. A "classifier," as used in this disclosure, is a process whereby computing device 104 derives from training data, a model known as a "classifier" for sorting inputs into categories or bins of data. A classifier utilizes a prior food preference input 148 as an input, and outputs a food profile 156. Computing device 104 trains classifier, utilizing training data. Training data may be obtained from records of previous iterations of a classifier, user inputs and/or questionnaire responses, expert inputs, and the like. A Naïve Bayes classifier 152, utilizes a family of algorithms to assign class labels to problem instances, represented as vectors of feature values, where class labels are derived from a finite set. A Naïve Bayes classifier 152 may generate classes, by calculating an estimate for a class probability from a training set. A Naïve Bayes classifier 152 may include generating a Gaussian Naïve Bayes classifier 152, that may be generated based on an assumption that continuous values associated with each class are distributed according to a normal or Gaussian distribution. A Naïve Bayes classifier 152 may include generating a multinomial Naïve Bayes classifier 152, where feature vectors represent the frequencies with which certain events have been generated by a multinomial. A Naïve Bayes classifier 152 may include generating a Bernoulli Naïve Bayes classifier 152, where features that are independent Boolean binary variables describe inputs.

With continued reference to FIG. 1, computing device 104 classifies a prior food preference input 148 to a food profile 156. A "food profile," as used in this disclosure, is a compilation of food elements 124 containing an associated datum indicating whether or not each food element is recommended for a user. A food profile 156 may contain food elements 124 that are similar to food elements 124 contained within a prior food preference input 148. For example, a prior food preference input 148 that contains a meal containing salmon may be classified to a food profile 156 that recommends other fish choices similar to salmon including Arctic char, Ocean trout, Amber Jack, Mackerel, Wahoo, Striped Bass, Milkfish, and Bluefish. A food profile 156 may contain food element 124 that may pair well with food element 124 contained within a prior food preference input 148. For example, a prior food preference input 148 that contains a chocolate cake may be utilized to recommend in a food profile 156 other desserts containing chocolate such as chocolate cupcakes, chocolate ice cream, and chocolate pudding. A prior food preference input 148 may be evaluated to determine food element 124 that a user will dislike based on ingredients contained within a prior food preference input 148. For example, a prior food preference input 148 that contains only vegetarian entrees may be utilized to classify the user to a food profile 156 that contains only vegetarian food element 124 recommendations. In yet another non-limiting example, a prior food preference input 148 that contains only lactose free dairy products may be utilized to classify the user to a food profile 156 that contains lactose free dairy products. Computing device 104 utilizes a food profile 156 to generate an ordered food element list. Food element 124 contained within a food profile 156 may be utilized to order food element 124. For example, a food profile 156 that contains vegan food element 124 may be utilized by computing device 104 to generate an ordered food element list that ranks vegan food element 124 higher than animal containing food element 124. In yet another non-limiting example, a food profile 156 that contains food element 124 of a certain ethnicity may be utilized by computing device 104 to generate an ordered food element list that ranks food element 124 matching the ethnicity higher than food element 124 of other ethnicities.

With continued reference to FIG. 1, computing device 104 is configured to create a food preference menu for a user wherein creating the food preference menu 160 includes grouping ordered food elements. A "food preference menu," as used in this disclosure, is a list of suggested meal items for a user. A food preference menu 160 may contain a list of specific meals, such as suggested meals for breakfast, lunch, dinner, and/or snacks. A food preference menu 160 may contain a list of food element 124 needed to prepare a particular food preference menu 160 item. For instance and without limitation, a food preference menu 160 may contain a recommended breakfast that contains millet served with coconut milk and topped with cinnamon, vanilla, and black currants. In yet another non-limiting example, a food preference menu 160 may contain a recommended dinner that includes teriyaki salmon served with white rice and topped with broccoli, red cabbage, carrots, green onions, avocado, lime, and sprinkled with sesame seeds. Computing device 104 may utilize an ordered food element list containing food element list rankings, to rank food preference menu 160. For instance and without limitation, a user with a symptomatic input 108 of gout may receive a food preference menu 160 that foods a first meal item such as halibut with baby potatoes ranked as having a neutral effect on a user's symptoms of gout, and a second meal item such as grilled portobello mushroom topped with caramelized onions and served on a bed of millet as having a positive effect on a user's symptoms of gout. Computing device 104 groups ordered food element 124 to create meals. In an embodiment, computing device 104 groups food element 124 by pairing a first food element 124 with a second food element 124. Pairing may include combining food element 124 based on taste, food preferences, known combinations, recipes, and the like. For example, computing device 104 may group a first food element 124 such as oysters with a second food element 124 such as kiwi fruit. In yet another non-limiting example, a first food element 124 such as shrimp may be recommended to be paired with a second food element 124 such as avocado, however for a user with a dislike of avocado, another food element 124 such as mango may be recommended instead. Computing device 104 may consult symptomatic database 112 to identify a user's food preferences and/or an ordered food list to determine food element 124 pairings. In an embodiment, a user may select one or more food preference menu 160 items that are of interest to the user and/or that the user would consume, and computing device 104 may generate a grocery ingredient list. A "grocery ingredient list," as used in this disclosure, is a list of food element 124 needed to prepare a food preference menu 160 item. A grocery ingredient list may be utilized by a user to shop for food element 124 such as in a grocery store or online when ordering groceries to be picked up or delivered.

With continued reference to FIG. 1, a food preference menu 160 may include a nourishment strategy. A "nourishment strategy," as used in this disclosure, is any nutritional plan recommended for a user. A nutritional plan may include a map of suggested meals assigned to certain meal slots, times, and/or days of the week. A nutritional plan may be generated over a certain period of time, such as a plan for a day, a week, a month, a year, and the like. In an embodiment, computing device 104 may utilize a nourishment strategy to generate a grocery ingredient list for a user based on the nourishment strategy.

Figure 2:
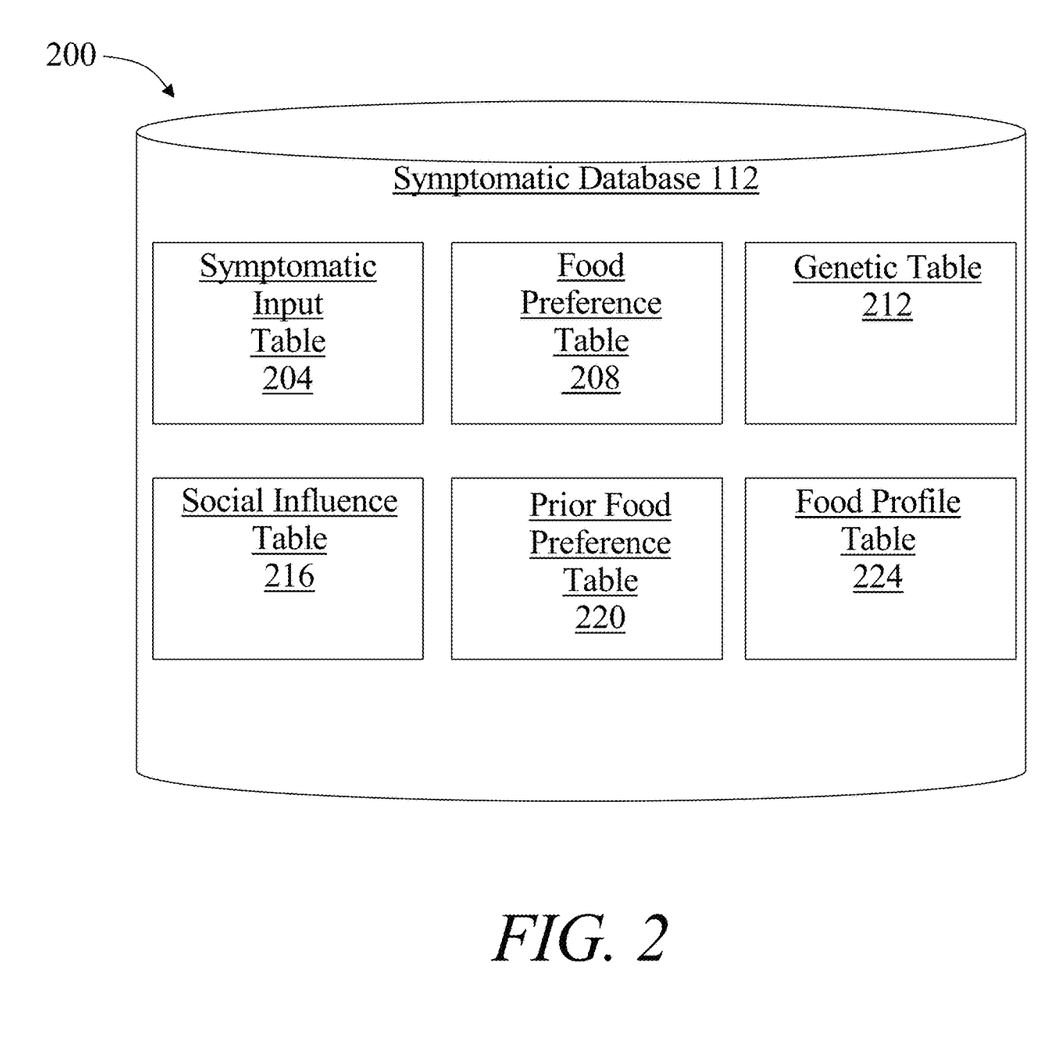
FIG. 2 is a block diagram illustrating an exemplary embodiment of a symptomatic database.

Referring now to FIG. 2, an exemplary embodiment 200 of symptomatic database 112 is illustrated. Symptomatic database 112 may be implemented as any data structure suitable for use as described above in more detail in reference to FIG. 1. One or more tables contained within symptomatic database 112 may include symptomatic input table 204; symptomatic input table 204 may include one or more symptomatic input 108 relating to a user. One or more tables contained within symptomatic database 112 may include food preference table 208; food preference table 208 may include one or more food preferences relating to a user. One or more tables contained within symptomatic database 112 may include genetic table 212; genetic table 212 may contain information relating to one or more genetically related food preferences 140 relating to a user. One or more tables contained within symptomatic database 112 may include social impact table 216; social impact table 216 may contain information relating to one or more social conduct factor 144. One or more tables contained within symptomatic database 112 may include prior food preference table 220; prior food preference table 220 may contain information relating to a user's prior food preference inputs 148. One or more tables contained within symptomatic database may include food profile table 224; food profile table 224 may include information pertaining to a user's food profile 156.

Figure 3:
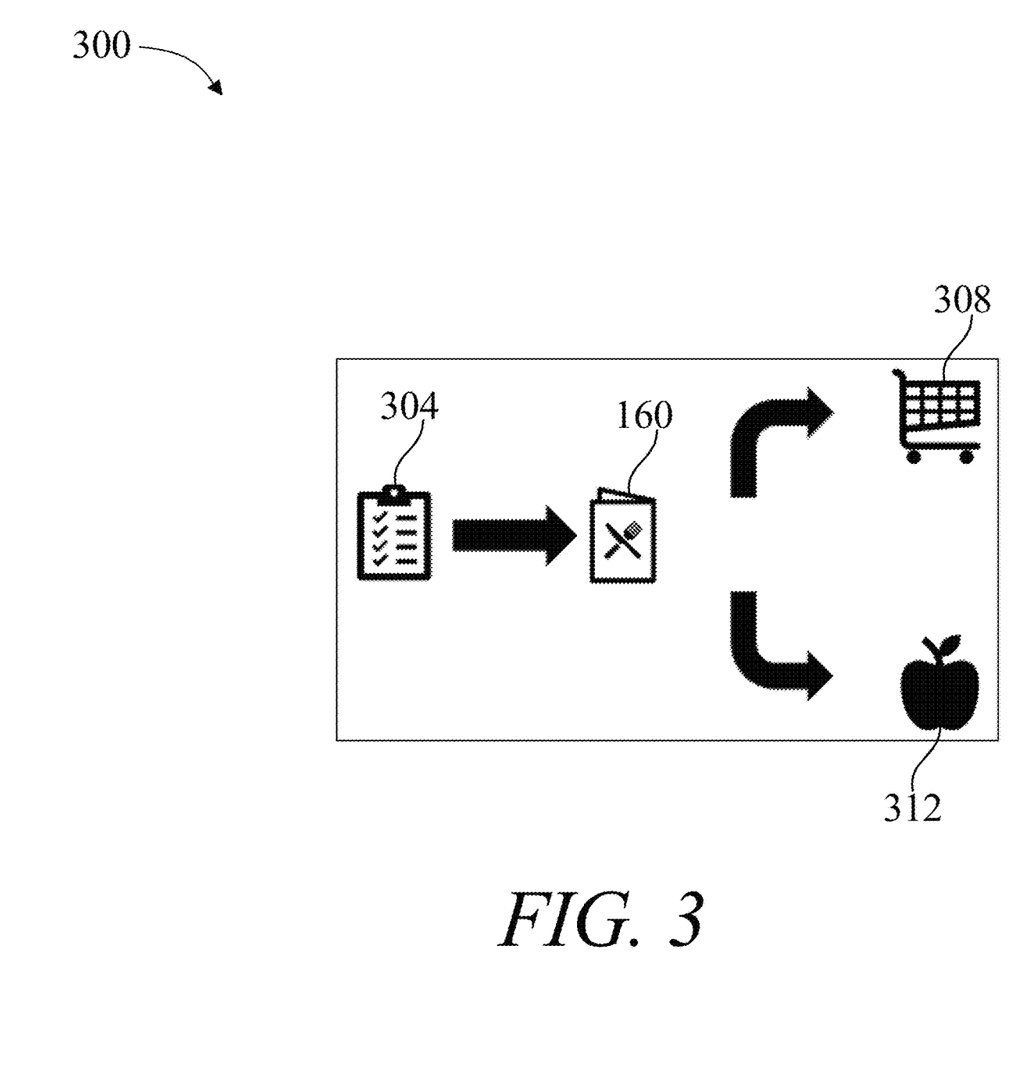
FIG. 3 is a diagrammatic representation of a food element list.

Referring now to FIG. 3, an exemplary embodiment 300 of food element list is illustrated. Computing device 104 generates an ordered food element list 304 ranking food element 124. An ordered food element list 304 may be generated utilizing any of the methodologies as described herein. Food element 124 contained within an ordered food element list 304 may be ranked utilizing symptomatic neutralizer 128, and the ability of a food element 124 to reduce and/or help exacerbate a symptomatic input 108. Food element 124 contained within an ordered foot item list 304 may also be ranked based on any food preference indicator 136, any genetically related food preference 140, and/or any social conduct factor 144. Computing device 104 utilizes an ordered food element list to create a food preference menu 160 for a user. A food preference menu 160 may contain suggested meal options for a user. For example, a food preference menu 160 may contain suggestions breakfast options, suggested lunch options, suggested dinner options, and/or any suggested snack options. Computing device 104 utilizes a food preference menu 160 to generate a grocery ingredient list 308. A grocery ingredient list may include any of the grocery ingredient lists as described above in more detail in reference to FIG. 1. For instance and without limitation, a user may select one or more suggested meals contained within a food preference menu 160 and utilize the suggested meals to generate a grocery ingredient list 308 to be utilized to purchase items in a grocery store or food store for example. Computing device 104 utilizes a food preference menu 160 to generate a nourishment strategy 312, including any of the nourishment strategies 312 as described above in more detail in reference to FIG. 1. A nourishment strategy may contain information mapping suggested meals to particular mealtimes over a specified period of time.

Figure 4:
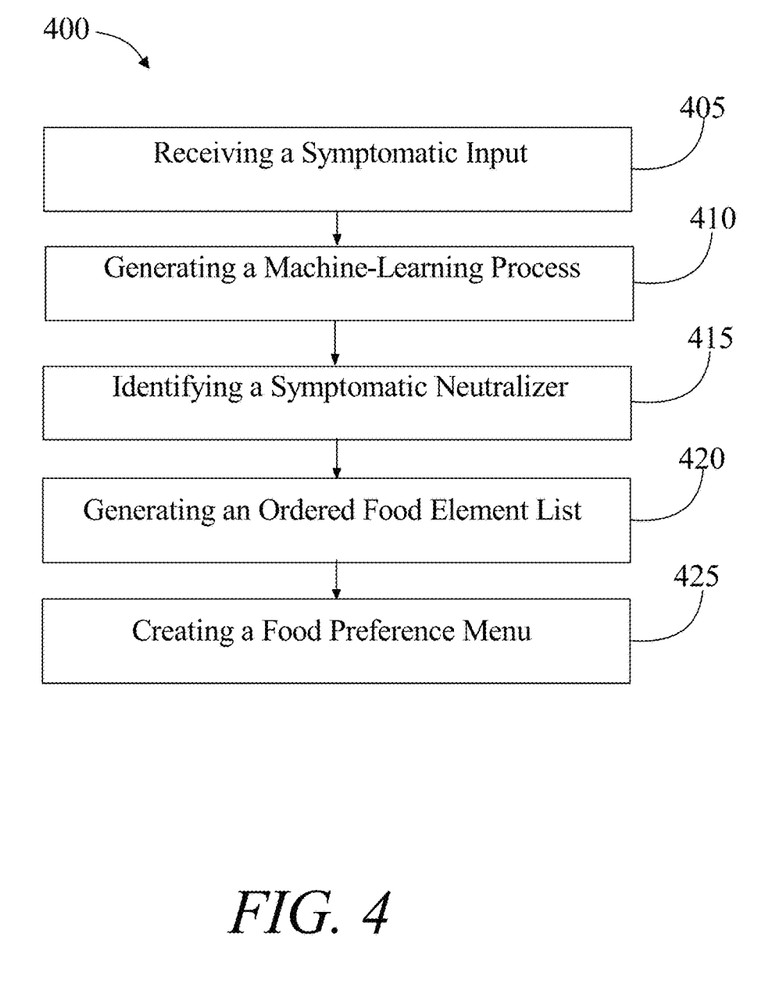
FIG. 4 is a process flow diagram illustrating an exemplary embodiment of a method of ordered food preferences accompanying symptomatic inputs.

Referring now to FIG. 4, an exemplary embodiment 400 of a method of ordered food preference 132 accompanying symptomatic input 108 is illustrated. At step 405, computing device 104 receives a symptomatic input 108 relating to a user. A symptomatic input 108 includes any of the symptomatic input 108 as described above in more detail in reference to FIG. 1. Computing device 104 may receive a symptomatic input 108 from a user device 116, utilizing any network methodology as described herein. In yet another non-limiting example, computing device 104 may receive a symptomatic input 108 from symptomatic database 112 as described above in more detail in reference to FIGS. 1-2. A symptomatic input 108 contains a description of a symptomatic complaint. A symptomatic complaint includes any of the symptomatic complaints as described above in more detail in reference to FIG. 1. A symptomatic complaint may contain a description of symptoms a user may be currently experiencing such as a headache, runny nose, and fatigue. A symptomatic complaint may contain a description of symptoms that come and go, such as nausea that occurs after eating. A symptomatic complaint may contain an element of previous physical data which may include any of the previous physical data as described above in more detail in reference to FIG. 1. For example, a symptomatic complaint may contain a description of a user's surgical history which specifies that a user has had three operations to try and mend a broken ankle. In yet another non-limiting example, a symptomatic complaint may contain a description of various allergies that a user has, such as an allergy to all corn containing products. A symptomatic complaint may contain a diagnosis, including any of the diagnoses as described above in more detail in reference to FIG. 1. For example, a symptomatic complaint may contain a user's self-reported diagnosis of rheumatoid arthritis. In yet another non-limiting example, a symptomatic complaint may contain a diagnosis that a user previously and that was previously cured and/or resolved. For example, a symptomatic complaint may contain a user's previous diagnosis of small intestinal bowel overgrowth that a user had for six months, that was resolved following a course of natural anti-microbials. In yet another non-limiting example, a symptomatic complaint may contain a description of a previous diagnosis a user had such as a *C-difficile* infection that was resolved upon completion of a course of antibiotics. Computing device 104 may store one or more symptomatic complaints within symptomatic database 112, as described above in more detail.

With continued reference to FIG. 4, at step 410, computing device 104 generates a machine-learning process wherein the machine-learning process is trained using a first training set that relates symptomatic inputs 108 to symptomatic neutralizers 128. A first training set may be obtained from any of the sources as described above in more detail in reference to FIG. 1. A machine-learning process 120 includes any of the machine-learning processes 120 as described above in more detail in reference to FIG. 1.

With continued reference to FIG. 4, at step 415, computing device 104 identifies a symptomatic neutralizer 128 based on a symptomatic input 108 using a machine-learning process 120. A symptomatic neutralizer 128 includes any of the symptomatic neutralizer 128 as described above in more detail in reference to FIG. 1. A symptomatic neutralizer contains an indication as to how much or how little a food element 124 helps alleviate or exacerbate a symptomatic input 108. For example, a symptomatic neutralizer 128 may indicate that a food element 124 such as garlic may help alleviate a symptomatic input 108 of a common cold, while a food element 124 such as foods containing dairy products may exacerbate the common cold. In yet another non-limiting example, a symptomatic neutralizer 128 may indicate that a food element 124 such as alcohol may worsen symptoms of nausea, while a food element 124 such as chicken broth may help alleviate symptoms of nausea.

With continued reference to FIG. 4, at step 420, computing device 104 generates an ordered food element list. An ordered food element list includes any of the ordered food element lists as described above in more detail in reference to FIG. 1. Computing device 104 generates an ordered food element list utilizing any of the methodologies as described above in more detail in reference to FIG. 1. Computing device 104 may generate an ordered food element list by ranking food element 124 that are most likely to help alleviate a symptomatic input 108, food element 124 that are neutral in alleviating a symptomatic input 108, and food element 124 that exacerbate a symptomatic input 108. Computing device 104 generates an ordered food element list utilizing symptomatic neutralizer 128 as described above in more detail in reference to FIG. 1. In an embodiment, computing device 104 may generate an ordered food element list utilizing a user food preference indicator 136, which may describe food element 124 that a user likes and/or dislikes. Computing device 104 utilizes a user food preference indicator 136 to rank food element 124 within an ordered food element list. For instance and without limitation, a user food preference indicator 136 that indicates a user prefers entrees containing fish over entrees containing meat, may be utilized to rank food element 124 that contain fish higher than food items containing meat, and symptomatic relief. For example, for a user with gout who prefers fish over meat, computing device 104 may utilize the information to rank fish very high, because the user enjoys eating it, and fish will help alleviate some symptoms of gout, while computing device 104 may rank meat much lower because it will exacerbate a user's symptoms and the user does not enjoy eating it. Computing device 104 may generate a food element list utilizing information pertaining to a social conduct factor 144, which may be stored in symptomatic database 112. A social conduct factor 144 includes any of the social conduct factor 144 as described above in more detail in reference to FIG. 1. A social conduct factor 144 may describe a social impact of a user's eating habits. For example, a social conduct factor 144 may contain information pertaining to any eating habits or eating behaviors that a user may have. For example, a social conduct factor 144 may indicate that a user dislikes eating breakfast and instead only has a cup of coffee in the morning. In yet another non-limiting example, a social conduct factor 144 may indicate that a user consumes a lot of French style food because the user grew up in France and developed eating habits similar to those of Fresh nationality.

With continued reference to FIG. 4, computing device 104 utilizes a genetically related food preference 140 for a user to generate an ordered food element list. A genetically related food preference 140 includes any of the genetically related food preference 140 as described above in more detail in reference to FIG. 1. A genetically related food preference 140 may be stored in symptomatic database 112 as described above in more detail in reference to FIG. 1. Computing device 104 evaluates a genetically related food preference 140 to determine food element 124 likes and/or food element 124 dislikes that may be genetically linked. For instance and without limitation, a genetically related food preference 140 may indicate that a user with a copy of an SLC2A2 gene may prefer foods that are sweeter, and as such, computing device 104 may rank food element 124 that contain sweet tasting foods such as berries, dark chocolate, and sweet potatoes as being more preferential for user. In such an instance, computing device 104 utilizes a genetically related food preference 140 to identify food element 124 that a user may prefer, as well as weighing in other factors that may affect the ranking of identified food element 124 within an ordered food element list.

With continued reference to FIG. 4, computing device 104 generates an ordered food element list utilizing a Naïve Bayes classifier 152. Computing device 104 receives a prior food preference input 148. A prior food preference input 148 includes any of the prior food preference input 148 as described above in more detail in reference to FIG. 1. A prior food preference input 148 contain a description of a meal a user previously consumed, such as a breakfast consisting of oatmeal topped with flaxseeds and berries. In yet another non-limiting example, a prior food preference input 148 may contain a description of a series or sequence of meals that a user previously consumed, such as all meals a user consumed for the past week, or all dinners that a user ate for a month. Information pertaining to a prior food preference input 148 may be stored within symptomatic database 112. Computing device 104 classifies using a Naïve Bayes classifier 152, a prior food preference input 148 to a food profile 156. A Naïve Bayes classifier, includes any of the Naïve Bayes classifier 152 as described above in more detail in reference to FIG. 1. A Naïve Bayes classifier 152 may be trained using a second training set relating prior food preference input 148 to food profile 156. A second training set may be obtained from any of the sources as described above in more detail in reference to FIG. 1. Computing device 104 generates an ordered food element list utilizing a food profile 156.

With continued reference to FIG. 4, at step 425, computing device 104 creates a food preference menu, wherein creating the food preference menu includes grouping ordered food elements. A food preference menu 160 includes any of the food preference menu 160 as described above in more detail in reference to FIG. 1. A food preference menu 160 may contain a list of specific meals, such as suggested meals for breakfast, lunch, dinner, and/or snacks. A food preference menu 160 may contain one or more recommended options for breakfast, one or more recommended options for lunch, one or more recommended options for dinner, and/or one or more recommended options for snacks. In an embodiment, computing device 104 may group a food element 124 to generate a food preference menu 160 by pairing a first food preference with a second food preference. For instance and without limitation, computing device 104 may pair a first food preference that contains a genetically related food preference 140 containing a user's genetic preference for salty foods, with a second food preference containing a user food preference indicator that contains a user's preference for shrimp, so create a food preference menu 160 that contains a menu item containing a salt and pepper shrimp entrée. Computing device 104 groups ordered food element 124 to generate a grocery ingredient list. A grocery ingredient list includes any of the grocery ingredient lists as described above in more detail in reference to FIG. 1. For example, a user may receive a transmission from computing device 104 to user device 116 containing a food preference menu 160 for a user. A user may select one or more menu items available within food preference menu 160 and transmit the selections back to computing device 104 from user device 116, utilizing any network methodology as described herein. Computing device may generate a grocery ingredient list, containing a list of ingredients that a user would need to acquire to prepare selected menu items. In an embodiment a grocery ingredient list may be modified to eliminate ingredients based on what ingredients a user may already have at home. In an embodiment, a grocery ingredient list may be displayed on remote device, so that a user could take the grocery ingredient list with them to a grocery store or place where ingredients may be sold, including any online grocery stores. Computing device 104 utilizes a food preference menu 160 to generate a nourishment strategy. A nourishment strategy includes any of the nourishment strategies as described above in more detail in reference to FIG. 1. A nourishment strategy may contain a list of suggested meals for a user, broken down by certain days or times.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
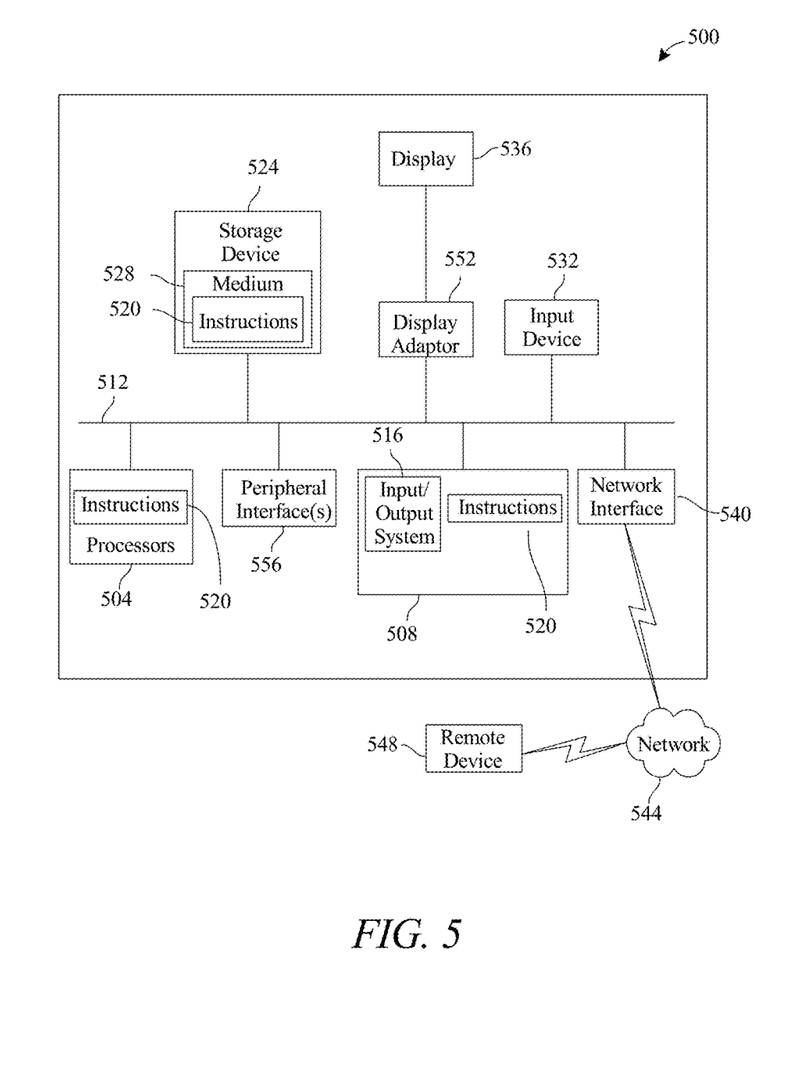
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for ordered food preferences accompanying symptomatic inputs, the system comprising a computing device, the computing device designed and configured to:
   receive a symptomatic input and a prior food preference input relating to a user, wherein the symptomatic input includes a description of a symptomatic complaint;
   classify, using a Naïve Bayes classifier, the prior food preference input to a food profile;
   generate a machine-learning process, wherein the machine-learning process is trained using a first training set relating symptomatic inputs to symptomatic neutralizers;
   identify a symptomatic neutralizer based on the symptomatic input using the machine-learning process, wherein the symptomatic neutralizer includes a numerical score;
   generate an ordered food element list as a function of the food profile, wherein the ordered food element list ranks food elements as a function of the symptomatic neutralizer; and
   create a food preference menu for the user wherein creating the food preference menu further comprising grouping the ordered food elements, and wherein the food preference menu includes a nourishment strategy, wherein the nourishment plan includes a nutritional plan comprising consuming the food preference menu for a period of time.

2. The system of claim 1, wherein the symptomatic input further comprises an element of previous physical data.

3. The system of claim 1, wherein the symptomatic input further comprises a diagnosis.

4. The system of claim 1, wherein the computing device is further configured to generate the ordered food element list utilizing a user food preference indicator.

5. The system of claim 1, wherein the computing device is further configured to:
   identify an element of data containing a genetically related food preference for the user; and
   generate the ordered food element list utilizing the genetically related food preference.

6. The system of claim 1, wherein the computing device is further configured to generate the ordered food element list utilizing a social conduct factor.

7. The system of claim 1, wherein the food preference menu further comprises a grocery ingredient list.

8. The system of claim 1, wherein the computing device is further configured to create the food preference menu as a function of pairing a first food preference with a second food preference.

9. A method of ordered food preferences accompanying symptomatic inputs the method comprising:
   receiving by a computing device, a symptomatic input and a prior food preference input relating to a user wherein the symptomatic input includes a description of a symptomatic complaint;
   classifying, by the computing device and using a Naïve Bayes classifier, the prior food reference input to a food profile;
   generating by the computing device, a machine-learning process, wherein the machine-learning process is trained using a first training set relating symptomatic inputs to symptomatic neutralizers;
   identifying by the computing device, a symptomatic neutralizer based on the symptomatic input using the machine-learning process, wherein the symptomatic neutralizer includes a numerical score;
   generating by the computing device, an ordered food element list as a function of the food profile, wherein the ordered food element list ranks food elements as a function of the symptomatic neutralizer; and
   creating by the computing device, a food preference menu for the user wherein creating the food preference menu further comprising grouping the ordered food elements, wherein the food preference menu includes a nourishment strategy, wherein the nourishment plan includes a nutritional plan comprising consuming the food preference menu for a period of time.

10. The method of claim 9, wherein the symptomatic input further comprises an element of previous physical data.

11. The method of claim 9, wherein the symptomatic input further comprises a diagnosis.

12. The method of claim 9, wherein generating the ordered food element list further comprises using a user food preference indicator.

13. The method of claim 9, wherein generating the ordered food element list further comprises:

identifying an element of data containing a genetically related food preference for the user; and generating the ordered food element list utilizing the genetically related food preference.

14. The method of claim 9, wherein generating the ordered food element list further comprises using a social conduct factor.

15. The method of claim 9, wherein the food preference menu further comprises a grocery ingredient list.

16. The method of claim 9, wherein creating the ordered food elements further comprises pairing a first food preference with a second food preference.

* * * * *